United States Patent [19] [11] 4,096,198
Mariconda et al. [45] Jun. 20, 1978

[54] INTEGRATED PROCESS FOR REGENERATING FLUOROSULFURIC ACID CATALYST

[75] Inventors: Albert J. Mariconda, Highland Lakes; Kenneth J. Reinman, Budd Lake; Ivan Mayer, Summit, all of N.J.

[73] Assignee: Exxon Research & Engineering Co., Linden, N.J.

[21] Appl. No.: 772,637

[22] Filed: Feb. 28, 1977

[51] Int. Cl.$^2$ .............................................. C07C 3/54
[52] U.S. Cl. .................... 260/683.47; 260/683.58; 252/411 R
[58] Field of Search ............. 260/683.47, 683.58, 260/683.62, 683.48

[56] References Cited

U.S. PATENT DOCUMENTS 3,887,635  6/1975  Parker et al. .............. 260/683.58
3,925,318  12/1975  Parker et al. .............. 260/683.58

Primary Examiner—George J. Crasanakis
Attorney, Agent, or Firm—John W. Ditsler

[57] ABSTRACT

An integrated process for regenerating a deactivated or partially deactivated alkylation catalyst comprising fluorosulfuric acid which comprises:
(1) contacting said fluorosulfuric acid with water to form an acid-water mixture, thereby converting at least a portion of the fluorosulfuric acid therein to hydrogen fluoride and sulfuric acid;
(2) removing at least a portion of the hydrogen fluoride from said acid-water mixture formed in step (1) by contacting same with a paraffin to form a gaseous phase containing hydrogen fluoride and said paraffin;
(3) cooling the gaseous phase formed in step (2) by contacting with liquid paraffin to condense a portion of the fluorosulfuric acid present in said gaseous phase, thereby forming a liquid phase and a gaseous phase each containing fluorosulfuric acid and hydrogen fluoride;
(4) treating the liquid and gaseous phases formed in step (3) with liquid sulfur trioxide to form a mixture comprising a liquid phase containing regenerated fluorosulfuric acid and a gas phase containing fluorosulfuric acid paraffin;
(5) separating the mixture formed in step (4) so as to form a liquid phase containing regenerated fluorosulfuric acid and a gas phase containing substantially pure paraffin;
(6) liquefying a portion of the gas phase separated in step (5) and using at least a portion thereof as the liquid paraffin in step (3); and
(7) using at least a portion of the gas phase separated in (5) as the paraffin in step (2). In a preferred embodiment, at least a portion of the regenerated fluorosulfuric acid separated in step (5) is recycled to the alkylation zone for use as an alkylation catalyst therein.

22 Claims, 1 Drawing Figure

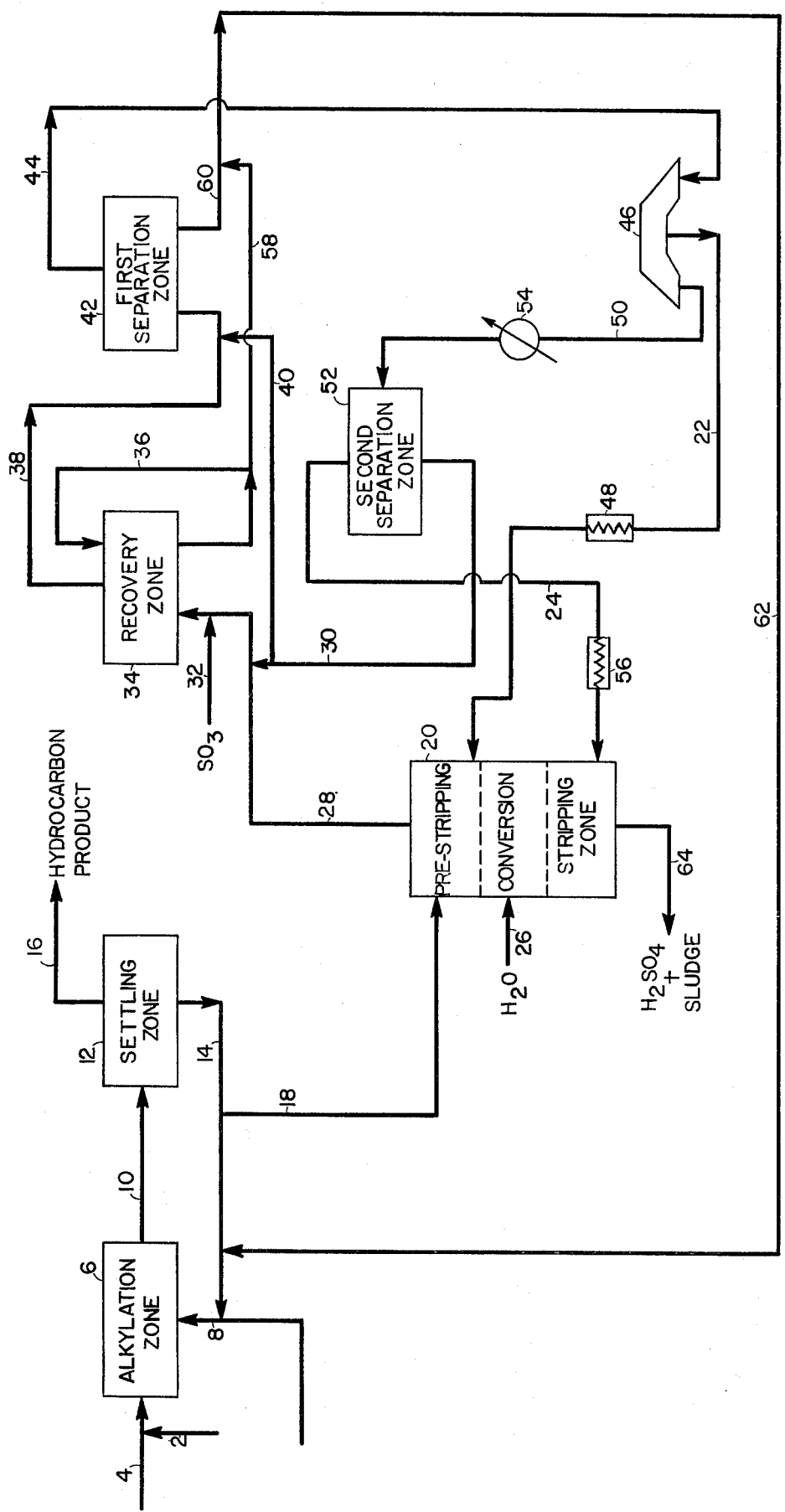

INTEGRATED PROCESS FOR REGENERATING FLUOROSULFURIC ACID CATALYST

BACKGROUND OF THE INVENTION

1. Field of the Invention

The present invention relates to a process for regenerating a catalyst of the type used in hydrocarbon conversion processes. More particularly, this invention relates to a process for regenerating a catalyst comprising fluorosulfuric acid, said catalyst having become at least partially deactivated due to the formation of stable catalytically inert species during contact with a hydrocarbon feedstock in an alkylation process.

2. Description of the Prior Art

It is well known in the prior art that as the alkylation reaction proceeds, an organic material will form and will accumulate in the fluorosulfuric acid catalyst phase. The material has been given a variety of names including red oil, sludge, organic sludge, acid oil and the like. This organic material is a natural by-product of acid-catalyzed hydrocarbon reactions such as occur during alkylation and has been described in the literature as a conjunct polymer (see Miron, S. and Lee, R. J., "Molecular Structure of Conjugated Polymers", J. Chem. Eng. Data, Vol. 8, p. 150–160 (1963), the disclosures of which are incorporated herein by reference. These conjunct polymers are complex mixtures of olefinic, conjugated cyclic hydrocarbons that may be formed from any type of hydrocarbon except aromatics. More specifically, they are believed to be cyclic polyolefinic hydrocarbons with a high proportion of conjugated double bonds, no two of which are in the same ring. Five membered ring systems predominate, but larger, and possibly also smaller, rings are believed to be present. The accumulation of this material will ultimately cause the activity of fluorosulfuric acid catalysts to decline until said catalysts cease to exhibit economic activity. In such cases, depending upon economic factors, the catalyst may be replaced or regenerated to restore desired activity levels.

One method for regenerating catalysts comprising fluorosulfuric acid has been suggested in U.S. Pat. No. 3,766,293, the disclosures of which are incorporated herein by reference. According to this method, an alkylation catalyst comprising fluorosulfuric acid, at least a portion of which has become deactivated, may be regenerated by (1) contacting said catalyst with water so as to convert at least a portion of the fluorosulfuric acid to hydrogen fluoride and sulfuric acid; (2) removing at least a portion of the hydrogen fluoride from said catalyst by contacting the same with a paraffin so as to form a hydrocarbon phase containing hydrogen fluoride; and (3) treating said hydrocarbon phase with sulfur trioxide to regenerate the fluorosulfuric acid. While the above method is effective in regenerating said catalyst, it is believed that the particular regeneration technique described herein below has certain advantages over that disclosed in U.S. Pat. No. 3,766,293, which heretofore have not been disclosed.

SUMMARY OF THE INVENTION

Now according to the present invention, an integrated process has been discovered for regenerating a deactivated or partially deactivated alkylation catalyst comprising fluorosulfuric acid, said deactivated or partially deactivated catalyst containing an organic sludge formed during said alkylation process, which comprises the method of:

(1) contacting said deactivated or partially deactivated fluorosulfuric acid with water to form an acid-water mixture, thereby converting at least a portion of the fluorosulfuric acid contained therein to hydrogen fluoride and sulfuric acid;

(2) removing at least a portion of the hydrogen fluoride from said acid-water mixture formed in step (1) by contacting same with a paraffin to form a gaseous phase containing hydrogen fluoride and paraffin and a liquid phase containing sulfuric acid and sludge;

(3) cooling the gaseous phase formed in step (2) by contact with liquid paraffin to condense a portion of the fluorosulfuric acid present in said gaseous phase, thereby forming a liquid phase and a gaseous phase each containing hydrogen fluoride and fluorosulfuric acid;

(4) treating the liquid and gaseous phases formed in (3) with at least a stoichiometric amount of liquid sulfur trioxide, based on hydrogen fluoride, to convert the hydrogen fluoride present therein to fluorosulfuric acid, thereby forming a mixture comprising a liquid phase containing regenerated fluorosulfuric acid and a gas phase containing fluorosulfuric acid and paraffin;

(5) separating the mixture formed in step (4) at a temperature and pressure sufficient to form a liquid phase containing regenerated fluorosulfuric acid and a gas phase containing substantially pure paraffin;

(6) liquefying a portion of the gas phase separated in step (5) and using at least a portion thereof as the liquid paraffin in step (3); and (7) using at least a portion of the non-liquefied portion of the gas phase separated in step (5) as the paraffin in step (2).

In a preferred embodiment, normal butane is the paraffin and at least a portion of the regenerated fluorosulfuric acid is recycled to the alkylation process.

The present invention has the advantage of providing an internally integrated process with a completely closed system with respect to the paraffin employed therein. Thus, by use of the present invention, regeneration of fluorosulfuric acid catalyst can be effected independent of the alkylation process such that regenerated catalyst can be made available during start-up and shut-down periods, as well as during normal operations. In addition, the present regeneration process is effected at relatively low temperatures, thereby minimizing the formation of coke and light gases (e.g., $C_1$–$C_3$ hydrocarbons) as well are reducing the sulfur trioxide requirements.

BRIEF DESCRIPTION OF THE DRAWING

The single FIGURE is a flow diagram illustrating a preferred embodiment of the present invention.

DETAILED DESCRIPTION OF THE INVENTION

Having thus described the invention in general terms, reference is now made to the FIGURE which shows an alkylation process using a catalyst system such as that described in U.S. Pat. No. 3,887,635, the disclosures of which are incorporated herein by reference. Such details are included as are necessary for a clear understanding of how the present invention may be applied in the regeneration of an alkylation catalyst comprising fluorosulfuric acid, said catalyst being at least partially deactivated. No intention is made to unduly limit the scope of the present invention to the particular configu- ration shown as variations obvious to those having ordinary skill in the art of alkylation and other unit operation processes are included within the broad scope of the present invention.

Referring now to the FIGURE, there is shown an olefin stream in line 2 which is, preferably, admixed with a paraffin stream in line 4 before introducing the combined stream into alkylation zone 6. If desired, however, the olefin and paraffin streams can be fed directly into alkylation zone 6. The olefin concentration in the feed ranges from 0.5 to 25 volume percent based on total feed and preferably below 10 volume percent. Translated into volume ratios, high volume ratios of paraffin to olefin ranging from 10:1 to 200:1 or higher are preferred, although somewhat lower ratios may be used, e.g., 3:1. Correspondingly high volume ratios of paraffin to olefin are also desired within the alkylation zone. Preferably, the paraffin/olefin ratio therein ranges from about 5:1 to 2000:1 or higher.

Suitable olefinic reactants include $C_2$–$C_{12}$ terminal and internal monoolefins such as ethylene, propylene, isobutylene, butene-1, butene-2, the pentenes (e.g., trimethylethylene) and similar higher monoolefinic hydrocarbons of either a straight chain or a branched chain structure. Preferably, the $C_2$–$C_6$ monoolefins are used, although the highly-branched $C_7$–$C_{12}$ monoolefins may also be used. The reaction mixtures may also contain small amounts of diolefins and other type hydrocarbons normally present in refinery hydrocarbon streams. Although it is desirable from an economic standpoint to use the normally gaseous olefins as reactants, normally liquid olefins may be used. Thus, reactable polymers, copolymers, interpolymers, crosspolymers, and the like, of the above-mentioned olefins, such as, for example, the diisobutylene and triisobutylene polymers, the codimer of normal butylene and isobutylene of butadiene and isobutylene, may be employed as an olefinic reactant. Mixtures of two or more of the olefins described above can be used as the process feedstock.

$C_2$, $C_3$, $C_4$ and/or $C_5$ olefin cuts from thermal and/or catalytic cracking units; field butanes which have been subjected to prior isomerization and/or partial dehydrogenation treatment; refinery stabilizer bottoms; spent gases; normally liquid products from sulfuric acid or phosphoric acid catalyzed polymerization and copolymerization processes; and products, normally liquid in character, from thermal and/or catalytic cracking units, are all excellent feedstocks for the present alkylation process. Such feeds are preferably dried to control excess water buildup, i.e., from about 5 to 15 wppm or less of water, before entering the alkylation zone.

The paraffinic feedstocks that can be reacted with the olefins desirably comprise straight and/or branched chain $C_4$–$C_{10}$ paraffins such as hexane, butane and the like, and preferably, $C_4$–$C_6$ isoparaffins such as isobutane, isopentane, isohexane and the like. While open chain hydrocarbons are preferred, cycloparaffins such as methylcyclopentane may also be used.

Returning to the FIGURE, a catalyst comprising fluorosulfuric acid and one or more moderators is shown being introduced into alkylation zone 6 via line 8. Generally, the moderator contains at least one oxygen atom per molecule and includes water, aliphatic and cycloaliphatic alcohols and ethers, aliphatic, cycloaliphatic and aromatic sulfonic and carboxylic acids and their derivatives, inorganic acids and other oxygen containing organic compounds. By the term "moderator" is meant a compound which, in combination with fluorosulfuric acid, produces a catalyst system of reduced acidity vis-a-vis the fluorosulfuric acid, and thereby decreases the probability of undesirable competing side reactions which have a detrimental effect on product quality, while increasing catalyst selectivity to desirable highly branched paraffinic products, thus resulting in high quality alkylate product. Various moderators that can be employed in the present catalyst system are shown at column 2, lines 38–67, column 3, lines 16–68, and column 4, lines 1–23 of U.S. Pat. No. 3,887,635.

Preferred catalyst moderators contain either a hydroxy group such as alcohols or a hydroxy group precursor, such as ethers which, it is speculated, can potentially cleave to form alcohols under the acidic conditions of the subject invention. Of these, the more preferred moderators are the alcohols and water, the most preferred being water. It is noted that the catalyst moderator and the fluorosulfuric acid can be premixed prior to introduction into the reactor, thereby forming the catalyst system. The catalyst may also be formed in situ.

The exact mechanism by which the moderator compounds effectuate increased catalyst selectivity while reducing competitive side reactions is not known. However, the active catalyst species employed herein is postulated to be an equilibrium mixture comprising several components. By way of illustration, it is speculated that the addition of water to fluorosulfuric acid, results in initial dissociation of the strong acid followed by hydrolysis:

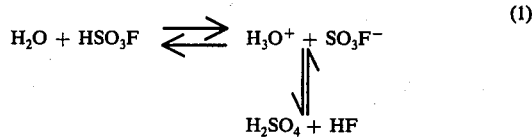

The equilibrium is believed to lie towards the right and, therefore, little, if any, free water should exist in the strong acid system. Similar mechanisms can be postulated for other moderators such as alcohols and ethers.

By the very nature of the postulated mechanism, it is clear that the manner in which the active catalytic system is formed is immaterial. Thus, in the above example, mixing HF and $H_2SO_4$ in equal molar amounts should result in the same catalyst system as would be obtained by mixing water with $HSO_3F$. The active catalyst system may also be formed by mixing HF, $H_2SO_4$ and $HSO_3F$ in appropriate amounts. Hence, when the catalyst system is described as "being formed from" a strong acid and a moderator, it is not meant to be limited to any one catalyst formation mode; rather, this description is used merely for convenience in providing a simple definition of the active catalyst system.

The amount of moderator used in forming the catalyst system is an important variable in the production of high quality alkylate. The desired amounts of moderator will vary dependent, in part, on the alkylation temperature. Thus, for example, at temperatures between about 0° to 40° F., useful amounts of moderator can range between about 5 and 45 mole % based on acid. In some instance, however, it may be desirable to use somewhat lower or higher amount of moderator, e.g., 50 mole % based on acid, where, for example, different catalyst activity or selectivity is desired.

At high alkylation temperatures, e.g., between about 40° and 100° F., increased amount of moderator may be desirable due to the increased strong acid activity. Thus, an amount of moderator ranging between about 50 and 100 mole % based on acid may be used at these higher temperatures. In fact, under appropriate conditions, these higher amounts of moderator may also be utilized at the lower temperatures disclosed hereinabove, if desired. A preferred catalyst is one formed from fluorosulfuric acid and from about 5 to 100 mole %, based on acid, of (1) water, (2) a $C_1$-$C_7$ saturated aliphatic monohydroxy or (3) a mixture of water and said alcohol.

Although the broad concentration ranges are generally independent of the type of moderator used, the preferred or optimal range will vary depending on the structure of the moderator, the reaction temperature, the concentration and nature of the olefin in the feed, the amount of organic sludge present, the olefin space velocity and the like.

In addition to being used in classical alkylation processes as hereinabove described, the catalyst system employed herein may also be used in self-alkylation processes. The $C_4$-$C_{16}$ branched chain olefins and $C_4$-$C_8$ isoparaffins are preferred reactants. The process is generally conducted in the liquid phase whereby the isoparaffin is dimerized and the olefin is sacrificed by being saturated, thus producing an alkylate-type product of high quality. Self-alkylation processes are generally described in U.S. Pat. No. 3,150,204. Undesired side reactions are minimized using these catalyst systems, thereby providing high yields of the desired products.

In general the amount of olefin contacted with the catalyst can range from about 0.05 to 1000 volumes of olenfin per hour per volume of catalyst inventory in the reactor (V/V/Hr.), i.e., olefin space velocity. Preferably, the olefin space velocity ranges from about 0.05 to 10.0 V/V/Hr., and still more preferably from about 0.05 to 1.0 V/V/Hr., e.g. 0.1 V/V/Hr. The volume % of total catalyst in the reaction mixture or emulsion (when liquid phase operations are used) in the alkylation zone can range from about 30 to 80 volume % based on total reaction mixture and preferably from about 50 to 70 volume %. The isoparaffin concentration, including alkylate, in the hydrocarbon phase (in a liquid phase process) can range from 40 to about 100 volume % based on the total volume of the hydrocarbon phase and preferably from 50 to 90 volume %. Such isoparaffin concentrations can be maintained by recycling unreacted isoparaffin to the alkylation zone.

The process may be carried out either as a batch or continuous type of operation, although it is preferred for economic reasons to carry out the process continuously. It has been generally established that in alkylation processes, the more intimate the contact between the feedstock and the catalyst the better the yield of saturated product obtained. With this in mind, the present process, when operated in either a batch or in a continuous manner, is characterized by the use of vigorous mechanical stirring or mixing of the reactants with the catalyst.

In continuous operations, as that of the embodiment shown in the drawing, the reactants may be maintained at sufficient pressures and temperatures to maintain them substantially in the liquid state and then continuously forced through dispersion devices into the alkylation zone. The dispersion devices may be jets, porous thimbles and the like. The reactants are subsequently mixed with the catalyst in alkylation zone 6 by conventional mixing means (not shown) such as mechanical agitators and the like. While the alkylation reaction can be carried out at a temperature within the range of from about $-80°$ to $+100°$ F., fairly low reaction temperatures, preferably within the range of from about $-80°$ to $+70°$ F., and most preferably within the range of from about $-20°$ to about $+40°$ F., are usually employed. Where the reaction is carried out at temperatures about $+10°$ F., or higher, it is necessary that the reaction be conducted under superatmospheric pressure, if the reactants and/or the catalyst are to be maintained substantially in a liquid state. Typically, the alkylation reaction is conducted at pressures varying from about atmospheric to about 300 psia.

In general, it is preferable to employ pressures sufficiently high to maintain the reactants in the liquid phase although a vapor phase operation is also contemplated. Autorefrigerated reactors and the like may be employed to maintain liquid phase operation. Although it is preferred to run the reaction neat, solvents or diluents may be employed if desired.

After allowing sufficient residence time for the reaction to progress, typically on the order from about one minute to one hour or more, the reaction mixture which contains hydrocarbon and deactivated or partially deactivated catalyst (often referred to as the "emulsion mixture") is withdrawn from the alkylation zone 6 vial line 10 and passed into a settling zone 12. The reaction mixture will separate in zone 12 into a heavy acid phase containing the fluorosulfuric acid, sulfuric acid, hydrogen fluoride and moderator (assumed to be water for the purpose of illustration in the following discussion), as well as organic sludge formed during said alkylation process, and a hydrocarbon phase containing the alkylate product along with smaller amounts of fluorosulfuric acid, hydrogen fluoride and water which are dispersed and/or dissolved therein. The acid phase is withdrawn from settling zone 12 via line 14 and at least a portion thereof can be recycled to alkylation zone 6 via line 8 or charged to another alkylation zone, if desired. The hydrocarbon phase is withdrawn from settling zone 12 via line 16.

The present invention will now be illustrated with reference to removing a portion of the fluorosulfuric acid from the deactivated or partially deactivated catalyst prior to contacting same with water (i.e., prestripping), as is disclosed in application Ser. No. 772,641, filed on the same date herewith. However, it should be clearly understood that while prestripping is a preferred embodiment of the present invention, this invention is equally applicable to regeneration processes which do not include prestripping, such as those disclosed in U.S. Pat. Nos. 3,766,293 and 3,476,759.

Referring again to the FIGURE, a purge stream of the heavy acid phase is shown being withdrawn from line 14 and being passed via line 18 into the upper portion of prestripping/conversion/stripping zone 20 and intimately contacted with a paraffin introduced via line 22 as well as by line 24. Preferred paraffins are $C_3$-$C_6$ paraffins, more preferably $C_4$ paraffins. Normal butane is the most preferred paraffin. As a result of said contacting, a portion, preferably a major portion, of both the hydrofluoric acid and the fluorosulfuric acid are stripped from said purge stream, thereby forming a gas phase containing paraffin, fluorosulfuric acid and hydrogen fluoride and a liquid phase containing fluorosulfuric acid, organic sludge and sulfuric acid as well as traces of hydrogen fluoride. The amount of stripping agent employed is that required to remove the desired amount of fluorosulfuric acid. It should be pointed out that hydrofluoric acid and sulfuric acid are present in streams 14 and 18 because the fluorosulfuric acid is partially dissociated when contacted with the moderator, e.g., water. If no moderator is employed, small amounts of water are normally introduced into the alkylation zone (e.g. with the feed) such that said partial dissociation will occur. Be that as it may, however, the present regeneration process is also applicable to a fluorosulfuric acid catalyst that has not been hydrolyzed.

The liquid phase then passes to the middle portion of zone 20 wherein it is contacted with water injected via line 26 in an amount sufficient to convert the fluorosulfuric acid to free hydrogen fluoride and sulfuric acid according to the reaction:

$$H_2O + HSO_3F \rightleftarrows H_2SO_4 + HF \uparrow + Heat \tag{2}$$

In one embodiment of the invention, it may be desirable to add up to a mole of water in excess of the stoichiometric amount required. Preferably, less than about 0.5 mole excess water is used. The resulting stream of water, hydrogen fluoride, sulfuric acid and organic sludge is then passed into the lower portion of zone 20 and intimately contacted therein with a paraffin introduced via line 24, thereby stripping hydrogen fluoride from said stream.

The particular temperature and pressure employed in zone 20 are, in general, determined by economic factors such as cost or availability of stripping agent, cost of $SO_3$, etc. Normally, zone 20 should be operated at a temperature above that at which the vapor pressure of fluorosulfuric acid becomes sufficiently low such that uneconomical amounts of stripping agent are required. It is also desirable to operate zone 20 at as high a temperature as possible because better stripping is obtained and less stripping agent is required. However, as disclosed in application Ser. No. 772,636, filed on the same date herewith, undesirable side reactions between the fluorosulfuric acid and acidic components in the catalyst (e.g. HF, $H_2SO_4$ and the like) and the hydrocarbon stripping agent becomes excessive at elevated temperatures, i.e. temperatures above about 250° F. Such reactions result in the formation of a polymer-like material, e.g. coke, that could "plug" the system. Thus, while elevated temperatures would normally be preferred, it has been found necessary, as disclosed in Ser. No. 772,636, to avoid contacting the acid components with the hydrocarbon stripping agent at temperatures in excess of 250° F. Therefore, as disclosed in Ser. No. 772,636, it is desirable that the temperature of zone 20 be maintained below 250° F and in the range of from about 120° to about 250° F, preferably in the range of from about 130° to about 210° F, and more preferably in the range of from about 140° to 170° F. Total pressure of zone 20 can also vary according to the economic factors mentioned above. In general, however, the total pressure will range from about atmospheric pressure to about 170 psia, preferably to about 120 psia, and more preferably from about 20 to about 90 psia.

A gas phase comprising paraffin fluorosulfuric acid and hydrofluoric acid passes from zone 20 via line 28 and is cooled by contact with a vaporizable liquid paraffin injected via line 30, thereby forming a partially condensed vapor phase, i.e. a mixture or combination of liquid phase and vapor phase, containing fluorosulfuric acid and hydrogen fluoride. The gas phase from zone 20 is cooled to a temperature between the freezing point and boiling point of sulfur trioxide. The liquid and vapor phases thus formed are then reacted with at least a stoichiometric amount of liquid sulfur trioxide, based on HF, which is introduced via line 32, so that at least a portion, preferably a major portion, more preferably substantially all, of the hydrogen fluoride present in said mixed phase is converted to fluorosulfuric acid according to the reaction:

$$HF + SO_3 \rightarrow HFSO_3 + heat \tag{3}$$

The regenerated fluorosulfuric acid thus formed may then be recovered from a mixture which comprises a liquid phase containing predominantly fluorosulfuric acid and a gas phase containing paraffin and fluorosulfuric acid.

A particularly preferred method for effecting said fluorosulfuric acid recovery is shown in the FIGURE and involves passing the mixture into a recovery zone 34 wherein said mixture is separated into a gas phase containing fluorosulfuric acid and paraffin and a liquid phase containing regenerated fluorosulfuric acid. Recovery zone 34 also allows the reaction between sulfur trioxide and hydrogen fluoride to go to completion. If desired, liquid fluorosulfuric acid may be recirculated via line 36 to aid in the above reaction and in the recovery of regenerated fluorosulfuric acid via recontacting.

In general, the recovery zone is operated at a temperature above the freezing point but below the boiling point of sulfur trioxide. It is important that the sulfur trioxide be introduced as a liquid. Typically, this corresponds to a temperature in the range of from about 80° to about 120° F, preferably from about 90° to about 110° F. Stabilized sulfur trioxide (containing added $BF_3$) may also be used. The pressure of the recovery zone is not critical and will, in general, range from atmospheric to no greater than that of zone 20. Typically, a major portion of the fluorosulfuric acid contained in gas phase 28 will be removed, i.e. recovered, in recovery zone 34 when said zone is operated at the temperature and pressure conditions noted above.

The gas phase substantially depleted in fluorosulfuric acid, e.g. less than 1.0 vol %, which contains predominantly paraffin exits from recovery zone 34 via line 38 and is contacted with liquid paraffin injected via line 40 thereby liquefying at least a portion of the fluorosulfuric acid remaining therein. This results in a stream comprising a mixture of both gaseous and liquid paraffin and liquid regenerated fluorosulfuric acid. Fluorosulfuric acid may also be present in the gaseous phase, typically in amounts less than 2000 wppm. The thus cooled stream is then passed into first separation zone 42 which is operated at a temperature such that substantially all of the fluorosulfuric acid present in stream 38 is liquefied. This requires relatively low temperatures, e.g. 10°–20° F, so as to minimize the amount of fluorosulfuric acid in the gaseous phase. Preferably, the fluorosulfuric acid thus formed will be substantially free of paraffin, e.g., will contain less than 10,000 ppm, preferably less than 1000 wppm, more preferably less than 100 ppm of paraffin. The pressure of separation zone 42 should be maintained above atmospheric but below that of recovery zone 34. This separation zone serves to form a gas phase containing substantially pure paraffin, e.g., less than 1000 ppm, preferably less than 500 ppm fluorosulfuric acid, and a liquid phase containing regenerated fluorosulfuric acid.

The gas phase comprising substantially pure paraffin is withdrawn from separation zone 42 via line 44 and passed to a compression zone, e.g. two stage compressor 46, wherein a portion, typically a major portion, of said stream is elevated to a pressure sufficient for the paraffin to be employed as the prestripping agent in the upper portion of zone 20. As shown in the FIGURE, it may be necessary to preheat the paraffin by heating means 48 prior to introduction into zone 20, depending upon the temperature following compression and the temperature of zone 20. The remaining paraffin is cooled after further compression to a temperature sufficient to condense at least a portion, preferably a major portion, more preferably substantially all of said paraffin, the exact temperature will vary with the specific paraffin employed as well as the temperature of the cooling medium, (e.g. water, air, etc.) employed in condensation zone 54.

The compressed paraffin is then passed via line 50 into a second separation zone 52 thereby forming a gas phase and a liquid phase, both phases containing substantially pure paraffin. In general, the paraffin is cooled to a temperature consistent with the pressure necessary to supply at least the amount of paraffin required to effect the degree of fluorosulfuric acid and hydrogen fluoride removal in the upper and lower portions of zone 20, respectfully, and the amount of liquid paraffin required in lines 30 and 40 to effect sufficient cooling. It is also desirable to minimize the amount of fluorosulfuric acid present in the stripping agent for the reasons discussed below. One method of satisfying these requirements would be to condense substantially all of the compressed paraffin present in line 50 via cooler 54, accumulate the condensate and throttle same to the temperature and pressure which will meet the desired liquid and stripping agent requirements noted above. However, any convenient technique known in the art for satisfying the liquid cooling and stripping agent requirements may be employed. Typically, second separation zone 52 is operated at a temperature ranging from about 45° to about 100° F and a pressure ranging from about 15 to about 60 psia. Typically, zone 54 will operate at a temperature ranging from about 95° to about 120° F and at a pressure sufficient to effect the desired degree of condensation, the exact conditions depending upon the particular gas being cooled, the particular cooling medium employed and the like.

The substantially pure gas phase is then withdrawn from zone 52 and injected via line 24 into the lower portion of zone 20 for use as the stripping gas. It is desirable to use a high purity stripping gas in this service because the lower portion of zone 20 should be substantially free; i.e. less than 100 wppm, preferably less than 20 wppm, more preferably less than 200 wppb, most preferably less than 20 wppb, of fluoride-containing compounds in order to produce a substantially fluoride-free sulfuric acid-sludge in line 64. This is desirable since the presence of fluoride in the sludge will deactivate the catalyst in a sulfuric acid regeneration plant. In contrast, the gas in lines 22 and 44 will, in general, have at least 100 wppm, typically from 100 to about 1000 wppm, of fluorosulfuric acid present therein, the exact amount being set by the temperature and pressure of zone 42. Liquid paraffin is withdrawn from separation zone 52 via line 30 and employed as the cooling agent mentioned above. It may also be necessary to preheat the paraffin gas from zone 52 by heating means 56 prior to introduction into zone 20. The gas in line 24 may be employed in either the upper or lower portions of zone 20. The gas in line 22 may be employed in a similar manner but is preferably employed in the upper portion of zone 20.

Regenerated fluorosulfuric acid which may contain negligible amounts of water (typically less than 100 wppm), is withdrawn from zones 34 and 42 via lines 58 and 60, respectively, to form line 62 and at least a portion thereof is combined with the recycle acid stream 14 for return to alkylation zone 6 via line 8. Sulfuric acid and the sludge formed during the alkylation process can be removed from the lower portion of zone 20 via line 64 and sent to sulfuric acid regeneration (now shown) for sludge removal and reconcentration, or it can be discarded. Alternately, the sulfuric acid sludge stream can be employed for removing dissolved and/or dispersed fluorosulfuric acid from hydrocarbon phase 16.

The prestripping/conversion/stripping zone is conventional equipment suitable for gas-liquid or liquid-liquid contacting and is available from various equipment vendors. As such, it does not form a part of this invention. However, Hastelloy B or C is normally employed although carbon steel may be used at lower temperatures with substantially no free water present.

The designations "prestripping/conversion/stripping zone", "recovery zone" and "separation zone" are not limited to any particular piece of equipment, as a variety of equipment known to one skilled in the art can be suitably employed, provided there results substantially pure streams of liquid and gaseous paraffin and a stream of regenerated fluorosulfuric acid. Similarly, the paraffin stripping and water addition steps may be effected in separate apparatus as is shown in application Ser. No. 772,641, filed on the same date herewith.

An example of regenerating a partially deactivated alkylation catalyst containing initially 20 moles of water per 100 moles of fluorosulfuric acid, said catalyst being at least partially dissociated into hydrofluoric acid and sulfuric acid, according to the flow diagram shown in the FIGURE, was calculated and is presented in Table 1. For this particular operation, isobutane was used as the light hydrocarbon stripping and cooling agent, and the various zones were operated at the following conditions.

|  | T, °F | P, psia |
|---|---|---|
| Prestripping;Conversion/stripping zone 20 | | |
| Upper Portion | 150 | 19.7 |
| Lower Portion | 150 | 34.7 |
| Recover zone 34 | 100 | 16.7 |
| First Separation zone 42 | 14 | 15.7 |
| Second Separation zone 52 | 64 | 40 |

In addition, the temperature of stream 50 after condensation zone 54 prior to separation in zone 52 is about 105°–110° F at 70 psia.

It should be pointed out that the temperature in first separation zone 42 should be sufficient to maintain two phases at the particular pressure employed. In general, this corresponds to about the dew point of the gaseous phase entering zone 42. The upper temperature in zone 42 is set by primarily economic consideration. Higher temperatures result in increased amounts of fluorosulfuric acid being present in gaseous phase leaving zone 42. This, in turn, will increase the requirements of stripping agent in zone 20 in order to effect the same degree of stripping. If sufficient fluorosulfuric acid is present in line 44, the effectiveness of stripping in zone 20 would be seriously impaired and could even be rendered inoperative. When isobutane is the paraffin, the temperature should be maintained in the range of from about 10° to about 20° F.

TABLE I

| Flow Rate[1] Stream No. | 18 | 22 | 24 | 26 | 28 | 30 | 32 | 38 | 44 | 50 | 58 | 60 | 64 |
|---|---|---|---|---|---|---|---|---|---|---|---|---|---|
| $HSO_3F$ | 19.4 | 0.4 | 2 wppb | — | 17.8 | 0.2 | — | 6.8 | 0.6 | — | 18.1 | 6.2 | — |
| HF | 4.8 | — | — | — | 6.8 | — | — | — | — | — | — | — | — |
| $H_2SO_4$ | 4.8 | — | — | — | — | — | — | — | — | — | — | — | 6.8 |
| $iC_4$[2] | — | 1896 | 164 | — | 2060 | 788 | — | 2335 | 2848 | 952 | — | — | — |
| Sludge | 1.2 | — | — | — | — | — | — | — | — | — | — | — | 1.2 |
| $H_2O$ | — | — | — | 2.0 | — | — | — | — | — | — | — | — | — |
| $SO_3$ | — | — | — | — | — | — | 6.8 | — | — | — | — | — | — |
| T, °F | 50 | 100 | 64 | 160 | 150 | 64 | 100 | 100 | 14 | 122 | 100 | 14 | 150 |
| P, psia | 20 | 27.7 | 40 | 30 | 19.7 | 40 | 150 | 16.7 | 15.7 | 84 | 16.7 | 15.7 | 34.7 |

[1] All flow rates are in moles/hour.
[2] Pure $iC_4$ assumed.

As previously noted, hydrocarbon phase 16 contains dissolved and/or dispersed fluorosulfuric acid, water, hydrogen fluoride from partial dissociation of the acid, and other acidic materials such as sulfur dioxide, etc. If desired, the acid materials which are dissolved and/or dispersed in hydrocarbon phase 16 can be effectively removed by scrubbing said hydrocarbon phase with sulfuric acid. The sulfuric acid is preferably concentrated, being 98.0 to 100% $H_2SO_4$ as limited by the freezing point of the acid, but somewhat more dilute acid (95–97.9%) can also be used without substantial detriment to the efficiency of the process. The manner of scrubbing may be by any conventional means, such as by passing the sulfuric acid and hydrocarbons through a mixing orifice, a countercurrent contacting tower or by injecting them into a centrifugal pump, etc., as long as intimate contact between the hydrocarbon phase and the sulfuric acid is attained. However, countercurrent staged operations are preferred. The ratio of acid to hydrocarbon is not critical, but can vary from about 5 to 95% of the hydrocarbon stream. The temperature for scrubbing generally ranges from about 20° to 100° F. but must be greater than the freezing point of sulfuric acid. The pressure may be any pressure from atmospheric to about 500 psig. The resulting phases are settled after contacting. The hydrocarbon phase containing alkylate product may undergo further treatment to remove trace amounts of any acid materials present therein. Fluorosulfuric acid present in the sulfuric acid phase thus settled may be removed therefrom by introducing the acid phase into the upper portion of zone 20, preferably into the middle portion of said zone.

It should be pointed out that the level of activity at which the fluorosulfuric acid catalyst should be regenerated is not only a matter of ability to catalyze the alkylation reaction, but also a matter of economics. For example, it may be desirable to regenerate a mildly deactivated catalyst to essentially fresh catalyst activity rather than allow the catalyst to be reduced to a much lower level of activity and be regenerated to fresh or to less than fresh activity. Thus, as used herein, the term "regeneration" or "regenerated" means recovering a fluorosulfuric acid catalyst that possesses a greater activity for alkylation than that possessed by the deactivated or partially deactivated catalyst. It should be understood that the regeneration process of the present invention is applicable to catalysts such as those defined above which have lost some degree of activity and that the regeneration may only partially restore the lost activity.

Although the present regeneration process has been discussed with reference to the alkylation process and catalyst described in U.S. Pat. No. 3,887,635, it should be understood that it is applicable to any alkylation process that employs fluorosulfuric acid (see for example U.S. Pat. Nos. 3,922,319 and 3,928,487, the disclosures of which are incorporated herein by reference), including those processes that form fluorosulfuric acid from a strong acid and a moderator, e.g. mixing sulfuric acid and hydrofluoric acid in appropriate amounts (see for example U.S. Pat. No. 3,956,418).

What is claimed is:
1. In an alkylation process which comprises:
(a) contacting an olefin with a paraffin in an alkylation zone under alkylation conditions and with a catalyst comprising fluorosulfuric acid to form a reaction mixture of fluorosulfuric acid catalyst phase containing an organic sludge formed during said process and a hydrocarbon phase containing alkylate product;
(b) separating said hydrocarbon phase containing alkylate product from said fluorosulfuric acid catalyst phase, the improvement which comprises regenerating said acid catalyst phase according to the following steps:
(c) stripping a portion of the fluorosulfuric acid from the acid catalyst phase separated in step (b) with a paraffin to form a stripped acid phase containing fluorosulfuric acid and said organic sludge and a gaseous phase containing paraffin and fluorosulfuric acid;
(d) contacting said stripped acid phase formed in step (c) with water to form an acid-water mixture, thereby converting at least a portion of the fluorosulfuric acid contained therein to hydrogen fluoride and sulfuric acid;
(e) stripping at least a portion of the hydrogen fluoride from said acid-water mixture formed in step (d) with a paraffin to form a gaseous phase comprising hydrogen fluoride and paraffin and a liquid phase comprising sulfuric acid and organic sludge;
(f) cooling the gaseous phases formed in step (c) and step (e) with liquid paraffin to a temperature between the freezing point and the boiling point of sulfur trioxide to form a first liquid-vapor mixture which comprises a liquid phase containing fluorosulfuric acid and hydrogen fluoride and a vapor phase containing hydrogen fluoride, fluorosulfuric acid and paraffin;
(g) treating the liquid-vapor mixture formed in step (f) with at least a stoichiometric amount of liquid sulfur trioxide based on hydrogen fluoride to convert the hydrogen fluoride present therein to fluorosulfuric acid, thereby forming a second liquid-vapor mixture which comprises a liquid phase containing regenerated fluorosulfuric acid and a gas phase containing fluorosulfuric acid and paraffin;

(h) passing the liquid-vapor mixture formed in step (g) into a first separation zone which is maintained at a temperature sufficient to form a liquid phase of regenerated fluorosulfuric acid and a gaseous phase containing paraffin and less than 1000 ppm fluorosulfuric acid;

(i) compressing the gaseous phase formed in step (h) to a pressure ranging between atmospheric and 170 psia to form a compressed gaseous paraffin;

(j) using a portion of the compressed gaseous paraffin formed in step (i) as the paraffin in step (c);

(k) passing that portion of the compressed gaseous paraffin not used in step (j) into a second separation zone which is maintained at a temperature between 45° and 100° F, thereby forming a liquid phase of substantially pure paraffin and a vapor phase of paraffin containing less than 100 ppm of fluoride-containing compounds;

(l) using the vapor phase formed in step (k) as the paraffin in step (e) and the liquid phase formed in step (k) as the liquid paraffin in step (f).

2. The process of claim 1 wherein the liquid phase of regenerated fluorosulfuric acid formed in step (g) and step (h) is recycled to said alkylation zone in step (a).

3. The process of claim 1 wherein the alkylation catalyst includes a moderator in an amount of about 5 to 100 mole %, based on acid, of (1) water, (2) a $C_1$-$C_7$ saturated aliphatic monohydroxy alcohol, or (3) a mixture of water and said alcohol.

4. The process of claim 3 wherein said moderator is water.

5. The process of claim 1 wherein the paraffin used for stripping is a $C_4$ paraffin.

6. The process of claim 1 wherein the acid catalyst phase of step (b) contains HF.

7. The process of claim 1 wherein the vapor phase formed in step (k) contains less than 20 wppm of a fluoride-containing compound.

8. The process of claim 1 wherein the contacting of step (a) is carried out at a temperature within the range from about −80° to about +100° F and the stripping of steps (c) and (e) is carried out at a temperature within the range from about 120° to about 250° F.

9. In an alkylation process which comprises:
(a) contacting an olefin with a paraffin in an alkylation zone under alkylation conditions and with a catalyst comprising fluorosulfuric acid to form a reaction mixture of fluorosulfuric acid catalyst phase containing an organic sludge formed during said process and a hydrocarbon phase containing alkylate product;
(b) separating said hydrocarbon phase containing alkylate product from said fluorosulfuric acid catalyst phase, said hydrocarbon phase containing a portion of the fluorosulfuric acid;
(c) washing said hydrocarbon phase with an acid comprising sulfuric acid thereby removing at least a portion of the fluorosulfuric acid from said hydrocarbon phase and separating a sulfuric acid phase containing said fluorosulfuric acid from said hydrocarbon phase containing the alkylate product, the improvement which comprises regenerating said acid catalyst phase according to the following steps:

(d) stripping a portion of the fluorosulfuric acid from the acid catalyst phase separated in step (b) with a paraffin to form a stripped acid phase containing fluorosulfuric acid and organic sludge and a gaseous phase containing said paraffin and fluorosulfuric acid;

(e) contacting said stripped acid phase formed in step (d) and the sulfuric acid phase separated in step (c) with water to form an acid-water mixture, thereby converting at least a portion of the fluorosulfuric acid contained therein to hydrogen fluoride and sulfuric acid;

(f) stripping at least a portion of the hydrogen fluoride from said acid-water mixture formed in step (e) with a paraffin to form a gaseous phase comprising hydrogen fluoride and paraffin and a liquid phase comprising sulfuric acid and organic sludge;

(g) cooling the gaseous phases formed in step (d) and step (f) with liquid paraffin to a temperature between the freezing point and the boiling point of sulfur trioxide to form a first liquid-vapor mixture which comprises a liquid phase containing fluorosulfuric acid and hydrogen fluoride and a vapor phase containing hydrogen fluoride, fluorosulfuric acid and paraffin;

(h) treating the liquid-vapor mixture formed in step (g) with at least a stoichiometric amount of sulfur trioxide based on hydrogen fluoride to convert the hydrogen present therein to fluorosulfuric acid, thereby forming a second liquid-vapor mixture which comprises a liquid phase of regenerated fluorosulfuric acid and a gas phase containing fluorosulfuric acid and paraffin;

(i) passing the liquid-vapor mixture formed in step (h) into a first separation zone which is maintained at a temperature sufficient to form a liquid phase containing regenerated fluorosulfuric acid and a gaseous phase containing paraffin and less than 1000 ppm fluorosulfuric acid;

(j) compressing the gaseous phase formed in step (i) to a pressure ranging between atmospheric and 170 psia to form a compressed gaseous paraffin;

(k) using a portion of the compressed gaseous paraffin formed in step (j) as the paraffin in step (d);

(l) passing that portion of the compressed gaseous paraffin not used in step (k) into a second separation zone which is maintained at a temperature between 45° and 100° F, threby forming a liquid phase of substantially pure paraffin and a vapor phase of paraffin containing less than 100 ppm of fluoride-containing compounds;

(m) using the vapor phase formed in step (1) as the paraffin in step (f) and the liquid phase formed in step (1) as the liquid paraffin in step (g).

10. The process of claim 9 wherein the catalyst includes a moderator in an amount of from about 5 to 100 mole %, based on acid, of (1) water, (2) a $C_1$-$C_7$ saturated aliphatic monohydroxy alcohol or (3) a mixture of water and said alcohol.

11. The process of claim 9 wherein the alkylation catalyst includes water as a moderator.

12. The process of claim 9 wherein the acid catalyst phase of step (b) contains HF.

13. The process of claim 9 wherein the paraffin used for stripping is a $C_4$ paraffin.

14. The process of claim 9 wherein the liquid phase comprising sulfuric acid and organic sludge of step (f) is employed to wash the hydrocarbon phase in step (c).

15. The process of claim 9 wherein the contacting of step (a) is carried out at a temperature within the range from about −80° to about +100° F and the stripping of step (d) and step (f) is carried out at a temperature within the range from about 120° to about 250° F.

16. In an alkylation process which comprises:
(a) contacting an olefin with a paraffin in an alkylation zone under alkylation conditions and with a catalyst comprising fluorosulfuric acid to form a reaction mixture of fluorosulfuric acid catalyst phase containing an organic sludge formed during said process and a hydrocarbon phase containing alkylate product;
(b) separating said hydrocarbon phase containing alkylate product from said fluorosulfuric acid catalyst phase, the improvement which comprises regenerating said acid catalyst phase according to the following steps:
(c) contacting at least a portion of the fluorosulfuric acid phase separated in step (b) with water to form an acid-water mixture, thereby converting at least a portion of the fluorosulfuric acid contained therein to hydrogen fluoride and sulfuric acid;
(d) stripping at least a portion of the hydrogen fluoride from said acid-water mixture formed in step (c) with a paraffin to form a gaseous phase comprising hydrogen fluoride and paraffin and a liquid phase comprising sulfuric acid and organic sludge;
(e) cooling the gaseous phase formed in step (d) with liquid paraffin to a temperature between the freezing point and the boiling point of sulfur trioxide to form a first liquid-vapor mixture which comprises a liquid phase containing fluorosulfuric acid and hydrogen fluoride and a vapor phase containing paraffin and hydrogen fluoride;
(f) treating the liquid-vapor mixture formed in step (e) with at least a stoichiometric amount of sulfur trioxide based on hydrogen fluoride to convert the hydrogen fluoride present therein to fluorosulfuric acid, thereby forming a second liquid-vapor mixture which comprises a liquid phase of regenerated fluorosulfuric acid and a gas phase containing fluorosulfuric acid and paraffin;
(g) passing the liquid-vapor mixture formed in step (f) into a first separation zone which is maintained at a temperature sufficient to form a liquid phase containing regenerated fluorosulfuric acid and a gaseous phase containing paraffin and less than 1000 ppm fluorosulfuric acid;
(h) compressing the gaseous phase formed in step (g) to a pressure ranging between atmospheric and 170 psia to form a compressed gaseous paraffin;
(i) using a portion of the compressed gaseous paraffin formed in step (h) as a portion of the paraffin in step (d);
(j) passing that portion of the compressed gaseous paraffin not used in step (i) into a second separation zone which is maintained at a temperature between 45° and 100° F, thereby forming a liquid phase of substantially pure paraffin and a vapor phase of paraffin containing less than 100 ppm of fluoride-containing compounds;
(k) using the vapor phase formed in step (j) as a portion of the paraffin in step (d) and the liquid phase formed in step (j) as the liquid paraffin in step (e).

17. The process of claim 16 wherein the hydrocarbon phase separated in step (b) is washed with an acid comprising sulfuric acid to remove at least a portion of the fluorosulfuric acid from said hydrocarbon phase, thereby forming a sulfuric acid phase containing said fluorosulfuric acid and said hydrocarbon phase containing the alkylate product, and adding said sulfuric acid phase containing said fluorosulfuric acid to said fluorosulfuric acid catalyst phase separated in step (b) to regenerate the fluorosulfuric acid present in said sulfuric acid phase.

18. The process of claim 16 wherein the catalyst includes a moderator in an amount of from about 5 to 100 mole %, based on acid, of (1) water, (2) a $C_1$–$C_7$ saturated aliphatic monohydroxy alcohol, or (3) a mixture of water and said alcohol.

19. The process of claim 16 wherein the paraffin used for stripping is a $C_4$ paraffin.

20. The process of claim 1 wherein the vapor phase formed in step (k) contains less than 20 wppb of a fluoride-containing compound.

21. The process of claim 9 wherein the vapor phase formed in step (l) contains less than 20 wppm of a fluoride-containing compound.

22. The process of claim 16 wherein the vapor phase of step (j) contains less than 20 wppm of a fluoride-containing compound.

* * * * *